US006946567B2

(12) United States Patent
Zhang et al.

(10) Patent No.: US 6,946,567 B2
(45) Date of Patent: Sep. 20, 2005

(54) SKELETAL ISOMERIZATION OF ALKYL ESTERS AND DERIVATIVES PREPARED THEREFROM

(75) Inventors: Shuguang Zhang, New Rochelle, NY (US); Zongchao Zhang, Norwood, NJ (US); Dale Steichen, Naperville, IL (US)

(73) Assignee: Akzo Nobel N.V., Arnham (NL)

( * ) Notice: Subject to any disclaimer, the term of this patent is extended or adjusted under 35 U.S.C. 154(b) by 1 day.

(21) Appl. No.: 10/339,437

(22) Filed: Jan. 9, 2003

(65) Prior Publication Data

US 2003/0191330 A1 Oct. 9, 2003

Related U.S. Application Data

(63) Continuation-in-part of application No. 10/177,405, filed on Jun. 21, 2002, now Pat. No. 6,831,184.
(60) Provisional application No. 60/369,415, filed on Apr. 2, 2002.

(51) Int. Cl.$^7$ ............................................. C07C 51/353
(52) U.S. Cl. ..................... 554/125; 554/224; 516/204; 502/60; 502/64
(58) Field of Search ................................. 554/125, 156, 554/184

(56) References Cited

U.S. PATENT DOCUMENTS

| | | | |
|---|---|---|---|
| 2,812,342 A | 11/1957 | Peters | 260/409 |
| 3,395,100 A | 7/1968 | Fisher et al. | 252/8.8 |
| 3,865,855 A | 2/1975 | Linn et al. | 260/413 |
| 4,371,469 A | 2/1983 | Foglia et al. | 260/405.6 |
| 4,795,573 A | 1/1989 | Tsumadori et al. | 252/8.8 |
| 4,831,006 A | 5/1989 | Aufdembrink | 502/242 |
| 4,973,431 A | 11/1990 | Struve et al. | 260/409 |
| 5,057,296 A | 10/1991 | Beck | 423/277 |
| 5,198,203 A | 3/1993 | Kresge et al. | 423/718 |
| 5,364,949 A | 11/1994 | Neuss et al. | 554/161 |
| 5,401,865 A | 3/1995 | Laufenberg et al. | 554/141 |
| 5,481,025 A | 1/1996 | Laufenberg et al. | 554/142 |
| 5,677,473 A | 10/1997 | Tomifuji et al. | 554/158 |
| 5,856,539 A | * 1/1999 | Hodgson et al. | 554/125 |
| 5,886,201 A | * 3/1999 | Bonastre et al. | 54/110 |
| 6,455,716 B2 | * 9/2002 | Kenneally et al. | 554/158 |

FOREIGN PATENT DOCUMENTS

| | | | |
|---|---|---|---|
| CN | 01135624.3 | 11/1996 | |
| EP | 0 306 237 | 3/1989 | ............ B01J/29/32 |
| EP | 0 683 150 | 11/1995 | ......... C07C/51/353 |
| EP | 074451 81 | 5/1997 | ......... C07C/51/353 |
| WO | 01/66507 | 9/2001 | ......... C07C/51/353 |

OTHER PUBLICATIONS

International Search Report for PCT/EP02/06080 dated Jul. 10, 2001.
Van dew Waal et al; *Synthesis of All–silica Zeolite Beta. J. Chem. Soc. Chem Commun.*, pp. 1241–1242 (1994).

D.H. McMahon et al.; *Characterization of Products from Clay Catalyzed Polymerization of Tall Oil Fatty Acids, Journal of the American Oil Chemists' Society*, vol. 51, Dec., 1974, pp. 522–527.

W.C. Ault et al.; *Branched Chain Fatty Acids and Sulfonated Derivatives; Journal of the American Oil Chemists's Society*, vol. 42, Mar., 1965, pp. 233–236.

Y. Nakano et al.; *Thermal Alteration of Oleic Acid in the Presence of Clay Catalysts with Co–Catalysts, Journal of the American Oil Chemists' Society*, vol. 62, No. 5, May, 1985, pp. 888–891.

D.V. Kinsman; *Isostearic and Other Branched Acids; Journal of the American Oil Chemists' Society*, vol. 56, Nov., 1979, pp. 823A–827A.

Yu Han, et a, *Hydrothermally Stable Ordered Hexagonal Mesoporous Aluminosilictes Assembled from a Triblock Copolymer and Performed Aluminosilicate Precursors in Strongly Acidic Media*, I Chemical Materials, 2002, 14, 1144–1148.

Liu et al. *Steam–Stable MSU–S aluminosilicate Mesostructures Assembled from Zeolite ZSM–5 and Zeolite Beta Seeds, Angew. Chem. Int. Ed.* 2001, 40, No. 7, pp. 1255–1258.

Zongtao Zhang, et al, *Strongly Acidic and High–Temperature Hydrothermally Stable Mesoporous Aluminosiicates with Ordered Hexagonal Structure, Angew. Chem. Int. Ed.* 2001, 40, No. 7, pp. 1258–1262.

Zongtao Zhang, et al, *Mesoporous Aluminosilicates with Ordered Hexagonal Structure Strong Acidity, and Extraordinary Hydrothermal Stability at High Temperatures, J. Am. Chem. Soc.*, 2001, 123, pp. 5014–5021.

Yu Liu, et al.*Steam–Stable Alumnosilicate Mesostructures Assembled from Zeolite tuype Y Seeds, J. Am Chem. Soc.* 2000, 122, pp. 8791–8792.

Yu Han, et al, *A Novel Method for Incorporation of Heteroatoms into the Framework of Ordered Mesoporous Silica Materials Synthesized in Strong Acidic Media, J. Phys. Chem. B* 2001, 105, pp. 7963–7966.

* cited by examiner

*Primary Examiner*—Deborah D. Carr
(74) *Attorney, Agent, or Firm*—Ralph J. Mancini

(57) ABSTRACT

The present invention relates to a process for the skeletal isomerization of unsaturated linear fatty acids to branched fatty acids which comprises contacting said unsaturated linear fatty acids with at least one large pore zeolite catalyst wherein said at least one zeolite catalyst comprises a material having a three dimensional channel structure having a pore diameter of at least 6.0 Å. In another embodiment, the invention relates to a process for the skeletal isomerization and hydrogenation of unsaturated linear fatty acids to saturated branched fatty acids which comprises contacting said unsaturated linear fatty acids in the presence of an acidic catalyst, wherein said acidic catalyst comprises a mesoporous crystalline phase having pore walls containing primary and secondary crystalline building unit structures.

14 Claims, No Drawings

SKELETAL ISOMERIZATION OF ALKYL ESTERS AND DERIVATIVES PREPARED THEREFROM

The present application is a continuation-in-part of U.S. application Ser. No. 10/177,405 filed Jun. 21, 2002, now U.S. Pat. No. 6,831,184, and claims priority of U.S. provisional application No. 60/369,415 filed Apr. 2, 2002.

FIELD OF THE INVENTION

The present invention generally relates to a process for the isomerization of alkyl esters with a catalyst to branched methyl esters and to derivatives prepared therefrom.

BACKGROUND OF THE INVENTION

Methyl esters are the building blocks for various compositions ranging from lubricants, polymers, solvents, cosmetics and the like. Branched alkyl esters offer a number of useful features due to their chain length and random branching. More specifically, they are useful as surfactants, oxidatively stable, have low crystallinity, and have a lower melt point than straight chain alkyl esters.

Long, straight chain saturated alkyl esters (C10:0 and higher) are solid at room temperature, which makes them difficult to process in a number of applications. Unsaturated long chain alkyl esters, however, are liquid at room temperature, so are easy to process, but are unstable because of the existence of double bond(s). Branched alkyl esters mimic the properties of the straight chain unsaturated alkyl esters in many respects, but do not have the disadvantage of being unstable. "Branched alkyl esters" means alkyl esters containing one or more alkyl side groups which are attached to the carbon chain backbone at any position. Therefore, branched alkyl esters are for many applications more desirable than straight chain alkyl esters. Commercial branched alkyl esters are not, however, naturally occurring materials.

A number of process are known for the production of branched methyl esters. For example, in the process of U.S. Pat. No. 5,856,539 an alkyl ester feed comprising unsaturated alkyl esters is contacted with a catalyst, characterized in that the catalyst comprises a material having a microporous structure.

U.S. Pat. No. 5,677,473 describes a process for preparing branched chain fatty acids or alkyl esters thereof which comprises subjecting unsaturated fatty acids having 10–25 carbon atoms or alkyl esters thereof to a skeletal isomerization reaction in the presence of water or a lower alcohol using a zeolite as a catalyst. The zeolite has a linear pore structure of a size small enough to retard dimerization and large enough to allow diffusion of the branched fatty acids or alkyl esters thereof.

U.S. Pat. No. 5,364,949 describes a process for the production of branched fatty acids and their esters which comprises reacting unsaturated fatty acids or esters thereof with aliphatic nonactivated olefins in the presence of layer silicates and active carbon.

However, all of these processes are plagued by low yield and/or a high rate of undesireable byproduct formation. Accordingly, there is a need for a new process that overcomes these disadvantages, i.e. a process for the preparation of branched alkyl esters from straight chain unsaturated alkyl ester feedstocks with a high conversion rate, an increased selectivity towards branched monomeric isomers and which employs a reusable catalyst.

SUMMARY OF THE INVENTION

The present invention generally relates to a process for the skeletal isomerization of unsaturated linear fatty acids and/or alkyl esters thereof to their branched counterparts. Said process comprises contacting said unsaturated linear fatty acids and/or alkyl esters with at least one large pore acidic catalyst having a three-dimensional channel structure. The present invention also relates to a process for the preparation of branched fatty acids from straight chain unsaturated fatty acid feedstocks with a strongly acidic and hydrothermally stable mesoporous aluminosilicate and aluminophosphate catalyst materials having mesopores of 15–500 Å and contain primary and secondary nanosized zeolite structural units in the walls that separate mesopores.

The invention also relates to various derivatives prepared from the branched fatty acids and/or alkyl esters prepared in accordance with the present invention.

DETAILED DESCRIPTION OF THE PRESENT INVENTION

The present invention generally relates to a process for the skeletal isomerization of unsaturated linear fatty acids and/or alkyl esters to their branched branched counterparts. The process comprises contacting said unsaturated linear fatty acids and/or methyl esters with at least one large pore acidic catalyst having a three dimensional channel structure.

In another embodiment, the present invention relates to a process for the preparation of branched fatty acids from straight chain unsaturated fatty acid feedstocks with a strongly acidic and hydrothermally stable mesoporous aluminosilicate and aluminophosphate catalyst materials having mesopores of 15–500 Å and contain primary and secondary nanosized zeolite structural units in the walls that separate mesopores.

The present process advantageously converts fatty acid and/or alkyl ester feedstock into a mixture that is rich in branched fatty acids and/or branched alkyl esters and low in oligomers. While the reaction products of the present process will generally comprise both saturated as well as unsaturated products, both are thus included in the invention, there is high selectivity towards the formation of branched fatty acids and/or alkyl esters.

The invention also relates to various derivatives prepared from the branched fatty acids and/or alkyl esters prepared in accordance with the present invention.

The acidic catalyst of the invention is characterized in that it comprises a material having a three dimensional pore structure wherein at least one of the channel structures has a pore size large enough to allow diffusion of the branched fatty acids and/or alkyl esters thereof. More particularly, at least one of the channel structures has a pore size large enough for the fatty acid and/or alkyl ester to enter the pore and access the internal active sites. Typically, this pore size is at least about 5.5 Å, preferably at least 6.0 Å. Catalysts of this type having a three-dimensional channel structure have higher activity and are not as readily deactivated by pore mouth blockages compared to catalysts having one and/or two dimensional channel structures.

Various acidic catalysts having the required three dimensional pore structure and size are known to the skilled artisan. Examples of acidic catalysts employable in the claimed process include but are not limited to zeolites, acidic clays, molecular sieves and the like.

Zeolites are crystalline aluminosilicates generally represented by the formula

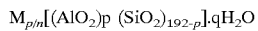

where M is a metal cation of groups IA including Hydrogen or IIA and n is the valency of this metal. Zeolites consist of a network of $SiO_4$ and $AlO_4$ tetrahedra linked together via shared oxygen atoms. Aluminum has a $3^+$ valency resulting in an excess negative charge on the $AlO_4$ tetrahedra, which can be compensated by cations such as $H^+$. When M is hydrogen the materials are Bronsted acidic, when M is for example Cs the materials are basic. Upon heating, Bronsted acidic hydroxyls condense creating coordinately unsaturated Al, which acts as a Lewis acid site. The acid strength, acid site density and Bronsted versus Lewis acidity are determined by the level of framework aluminum. The ratio of silica/alumina can be varied for a given class of zeolites either by controlled calcination, with or without the presence of steam, optionally followed by extraction of the resulting extra framework aluminum or by chemical treatment employing for example ammonium hexafluorosilicate.

As zeolite frameworks are typically negatively charged, the charge balancing cations related to this invention include monovalent cations such as $H^+$, $Li^+$ and the like, divalent cations such as $Mg^{2+}$, $Zn^{2+}$ and the like and trivalent cations such as $Ln^{3+}$, $Y^{3+}$, $Fe^{3+}$, $Cr^{3+}$ and the like. The framework composition of the three-dimensional zeolites may contain other elements in addition to Al and Si, such as, for example, P, Ti, Zr, Mn, and the like. Although any zeolite meeting the parameters of this embodiment of the present invention can be employed, faujasite (e.g. Y zeolite), Beta zeolite, Offeretite and the like are particularly well suited for the present process. The Si/Al ratio of the zeolites can vary depending on the particular zeolite employed provided that the skilled artisan understands that a ratio which is too low will result in more by-products and a ratio which is too high will lower the activity of the zeolite. In most cases the Si/Al ratio of the zeolites is at least 2, up to at least 20 and higher. For example, the Si/Al ratio for Beta zeolite may be from about 25-75 while that for Y zeolite can be from 2 to about 80.

Zeolites employable in the present process comprise a three-dimensional pore structure wherein at least one channel structure has a pore size large enough to allow diffusion of the branched fatty acids and/or alkyl esters thereof. In general, the larger the number of oxygen atoms in the ring opening, the larger the pore size of the zeolite. But this size is also determined by the structural shape of the ring. Zeolite materials having a three dimensional channel structure and a pore size of at least about 6.0 Å can generally be employed in the process of the invention. Such pore structures having a pore size of at least about 6.0 Å generally comprise 10 and/or 12 membered rings, or even larger rings in their structures.

It is known that zeolites having a three dimensional channel structure can be formed by zeolites having one dimensional channel with certain mineral acids such as nitric acid, hydrochloric acid and the like, and/or certain organo-carboxylic acids such as acetic acid and oxylic acid and the like. Other methods for generating zeolites with a three dimensional channel structure are known to the skilled artisan.

In another embodiment, the invention contemplates a process the invention utilizes mesoporous aluminosilicates. However, other mesoporous materials based on other materials such as those comprising transition metals and post transition metals can also be employed. Catalytic materials such as those employable in the context of the present invention are described in Angewandte Chemie Int. Ed. (7, 2001, 1258), J. Am. Chem. Soc. (123, 2001, 5014), J. Phys. Chem. (105, 2001, 7963), J. Am. Chem. Soc. (122, 2000, 8791), Angew. Chem. Int. Ed. (40, 2001, 1255), and Chem. Mater. (14, 2002, 1144) and in Chinese Patent Application No. 01135624.3, which are incorporated herein by reference.

Generally, the synthesis of the mesoporous aluminosilicates and aluminophosphates of the present invention involves the preparation of primary and secondary zeolite building unit precursors, which are subsequently assembled to stable mesoporous zeolites in the presence of surfactant or polymeric templates. Mesoporous zeolites derived from this invention have similar acidity, thermal and hydrothermal stability as conventional zeolites, and also have high catalytic activity.

As an example, highly ordered hexagonal mesoporous aluminosilicates (MAS-5) with uniform pore sizes were synthesized from an assembly of preformed aluminosilicate precursors with cetyltrimethylammonium bromide (CTAB) surfactant. Choice of surfactant is not a limiting feature as most quaternary ammonium salts, phosphonium salts, anionic and non-ionic surfactants, and polymers which form micellar structures in solution are effective. Other examples include, but are not limited to cetyltrimethylphosphonium, octyidecyltrimethylphosphonium, cetylpyridinium, myristyltrimethylammonium, decyltrimethylammonium, dodecyltrimethylammonium, dimethyldidodecylammonium, fatty alkylamines, fatty acids, and mixtures thereof.

The aluminosilicate precursors were obtained by heating aluminosilica gels from the aqueous hydrolysis of aluminum and silicon precursors. As previously mentioned, the present invention is not limited to Al and Si precursors, and other precursors such as certain transition metal candidates can be employed. The aluminosilicate gels are heated at 80°–400° C. for 2–10 hours. The gels had a $Al_2O_3/SiO_2/TEAOH/H_2O$ molar ratio of 1.0/7.0–350/10.0–33.0/500–2000. Mesoporous MAS-5 shows extraordinary stability in both boiling water and steam. Additionally, temperature-programmed desorption of ammonia shows that the acidic strength of MAS-5 is much higher than that of conventional mesoporous materials and is comparable to that of microporous Beta zeolite. Analysis and testing of the materials of the present invention suggest that MAS-5 consists of both mesopores and micropores and that the pore walls of the MAS-5 contain primary and secondary structural building units similar to those of microporous zeolites. The unique structural features of the mesoporous aluminosilicates of the present invention are believed to be responsible for the observed strong acidity and high thermal stability of the mesoporous mesoporous aluminosilicates of well ordered hexagonal symmetry.

Additionally, the scope of the present invention is not limited to zeolites in general, or to a particular zeolite, as materials other than zeolites can be employed in the context of the present invention. Zeolites are, however, a preferred material to be employed and the use of any known or yet to be discovered zeolites in the formation of the mesoporous materials of the present invention is included within the scope of the present invention. More particularly, using precursors of other zeolite structures, one of ordinary skill in the art could readily tailor make mesoporous zeolites containing the structural features of the particular zeolite chosen. Examples of zeolites which can be employed in the context of the present invention include, but are not limited to, zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, aluminophosphates including but not limited to VPI-5 and the like, and mixtures thereof, and/or zeolitic materials having the following framework structures: AEL, AFO, AHT, BOG, CGF, CGS, CON, DFO, FAU, FER, HEU, AFS, AFY, BEA, BPH, CLO, EMT, FAU, GME, MOR, MFI, and the like.

It is known that the aluminosilicates and/or aluminophosphates employable in the context of the present invention can be metal containing, or non-metal containing. Zeolites may contain elements such transition metals, post transition metals, Ln series and the like. Specific examples include, but are not limited to B, Ti, Ga, Zr, Ge, Va, Cr, Sb, Nb, and Y.

Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the fatty acid feedstock is contacted with the catalyst for a period of at least 30 minutes and reaction times of 1–16 hours are typical. An even longer period could be used if the process is operated at a lower temperature.

In general, the amount of catalyst employed in the process according to the invention is between 0.5 and 30% by weight when the process is carried out in batch or semibatch process, based on the total reaction mixture. In another embodiment the amount of catalyst used between 2.5 and 10% by weight. In still another embodiment the catalyst amounts are between 3 and 7% by weight.

The processes of the present invention can be performed both in batch and fixed bed continuous processes. Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the feedstock is contacted with the catalyst for a period of at least 30 minutes and reaction times of 1–16 hours are typical. An even longer period could be used if the process is operated at a lower temperature.

In general, the amount of catalyst employed in the process according to the invention is between 0.5 and 20% by weight, based on the total reaction mixture. In another embodiment the amount of catalyst used between 2.5 and 10% by weight. In still another embodiment the catalyst amounts are between 3 and 7% by weight.

When a continuous flow reactor is employed, the weight hour space velocity is between 0.1 and 25. Weight hour space velocity is defined as the weight of feed in grams passing over one gram of catalyst per hour.

Additionally, it has been found that by using a catalyst system according to this invention it is possible to reuse the catalyst. In some cases it may be desired to add fresh catalyst while optionally removing a part of the spent catalyst, and in other cases regeneration of the catalyst may be desired. Regeneration can be effected by various methods know to the skilled artisan. For example, regeneration can be accomplished by utilizing controlled oxidative regeneration and/or by washing with a solvent.

Typical feedstocks comprise fatty acids and esters derived from natural fats and oils. Such feedstocks are predominantly unsaturated linear alkylcarboxylic acids, related esters or mixtures thereof, optionally containing other organics. Since the present process is designed for isomerization or conversion of unsaturated fatty acids and/or alkyl esters into their branched counterparts, it is beneficial if the comprises of at least about 30% by weight of said unsaturated fatty acids and/or alkyl esters. In another embodiment, the feedstock comprises at least 50% by weight of unsaturated fatty acids and/or alkyl esters. Any unsaturated and/or polyunsaturated fatty acid and/or alkyl esters, or mixtures thereof is suitable as a feedstock in accordance with the present invention. In one embodiment, the feedstock comprises oleic acid as the unsaturated fatty acid and/or the alkyl ester of oleic acid in an amount of at least 40% by weight, preferably at least 70% by weight.

The invention also relates to the branched fatty acids and alkyl esters prepared by the processes described herein. Additionally, the invention contemplates all derivatives prepared from branched fatty acids and alkyl esters prepared by the processes described herein.

Fatty acid alkyl esters and fatty acids are versatile building blocks and conversion of these materials into a wide variety of other surfactants is possible. Some examples of the type of reactions possible are listed below. From these starting materials it is possible to produce non-ionic, anionic and cationic surfactants, all of which is within the scope of the present invention.

The branched fatty acid alkyl esters and fatty acids products of the present invention can be utilized as starting materials to prepare the same derivatives as their linear counterparts. For example, the branched alkyl esters of the present invention are readily converted into fatty acid glucamides and glycerol esters. Alkylation of polyhydridic molecules is possible. An example of this type of reaction would be reaction of a branched methyl ester with sucrose to prepare sucrose esters. Conversion of branched alkyl esters to alpha sulfonates is known. For example, branched fatty acid ester sulfonates (FAES) can be produced from branched methyl esters by sulfonation, followed by bleaching and neutralization. Branched fatty acid alkyl esters can also be converted into other branched alkyl esters by a transesterification reaction. In most cases, the smaller molecular weight alcohol is removed from the reaction mixture forcing the reaction to the desired products.

Branched fatty acids undergo many of the same reactions their linear counterparts as well as linear and branched fatty acid alkyl esters. For example, the branched fatty acid of the present invention may be converted into its' soap form by neutralization with a base. N-acyl sarcosinates can be prepared from reaction of the branched fatty acid of the present invention fatty acid or its derivatives with sarcosine. Acylated protein hydrolysates are prepared by acylation of protein hydrolysates with branched fatty acids or acid chlorides. The hydrolysates are variable in composition, depending on how they are prepared. These are mild surfactants used in often in personal care formulations. 2-Sulfoethyl esters of branched fatty acids, also known as acyl isethionates, are excellent surfactants. This family tends to be mild to the skin and hard water tolerant. Amido propyl amine and derivatives are prepared from the fatty acid or fatty acid alkyl ester. This family of surfactants has seen commercial application in laundry detergents, dishwashing liquids and many personal care formulations. Condensation of a fatty acid alkyl ester or fatty acid with an alkanolamine results in the formation of an alkanolamide. The alkanolamide and it derivatives have a variety of uses commercially depending on its specific chemical structure. Ethoxylated alkanolamides are used as compatibilizers in formulations. Many alkanolamides and derivatives are used as thickeners and foamers. Branched fatty acids can be alkoxylated with ethylene oxide, propylene oxide and butylenes oxide to make a useful family of non-ionic surfactants. Branched fatty acids can be converted into nitriles which are the building blocks for a large variety of cationic and amine surfactants. Branched fatty acids acan also be used in a reaction to prepare esteramines which are quaternized, esterquats. The major use of esterquats is in household fabric softeners.

Conversion of the branched alkyl esters and branched fatty acids into branched alcohols can also be done. The alcohol is another building block to prepare other types of surfactants. Alcohols are used to prepare alkyl polyglycosides (APGs). These materials offer a hydrophile based on a natural sugar. Conversion of the alcohol into amines and quaternaries occurs readily and is a commercially important reaction in the preparation of cationic surfactants. Non-ionic surfactants are prepared by alkoxylation of alcohols. Common alkoxylation agents are ethylene oxide, propylene oxide and butylene oxide. Conversion of alcohols (with or without alkoxylation) to alcohol sulfates is a commercially important process. The use of alcohol sulfates in laundry is increasing especially in Europe. Other areas of use include shampoos, textile processing and emulsion polymerization. Alcohols can also be converted in phosphate esters. Both mono and di phosphate esters can be favored depending on the reaction conditions. Polyalkoxycarbonates are produced by the reaction of sodium chloroacetate with an alcohol ethoxylate, or from acrylic acid and an alcohol ethoxylate. These can also be made by direct oxidation of the alcohol ethoxylate under carefully controlled conditions.

The aforementioned description is merely illustrative and not intended to limit the scope of the invention. Accordingly, one of ordinary skill in the art would readily recognize that the branched products of the present invention, like their linear counterparts, can be readily employed as starting materials in the preparation of numerous derivatives as illustrated by the following chart. Any and all of the derivatives prepared from the novel products of the present invention are within the scope of the present invention.

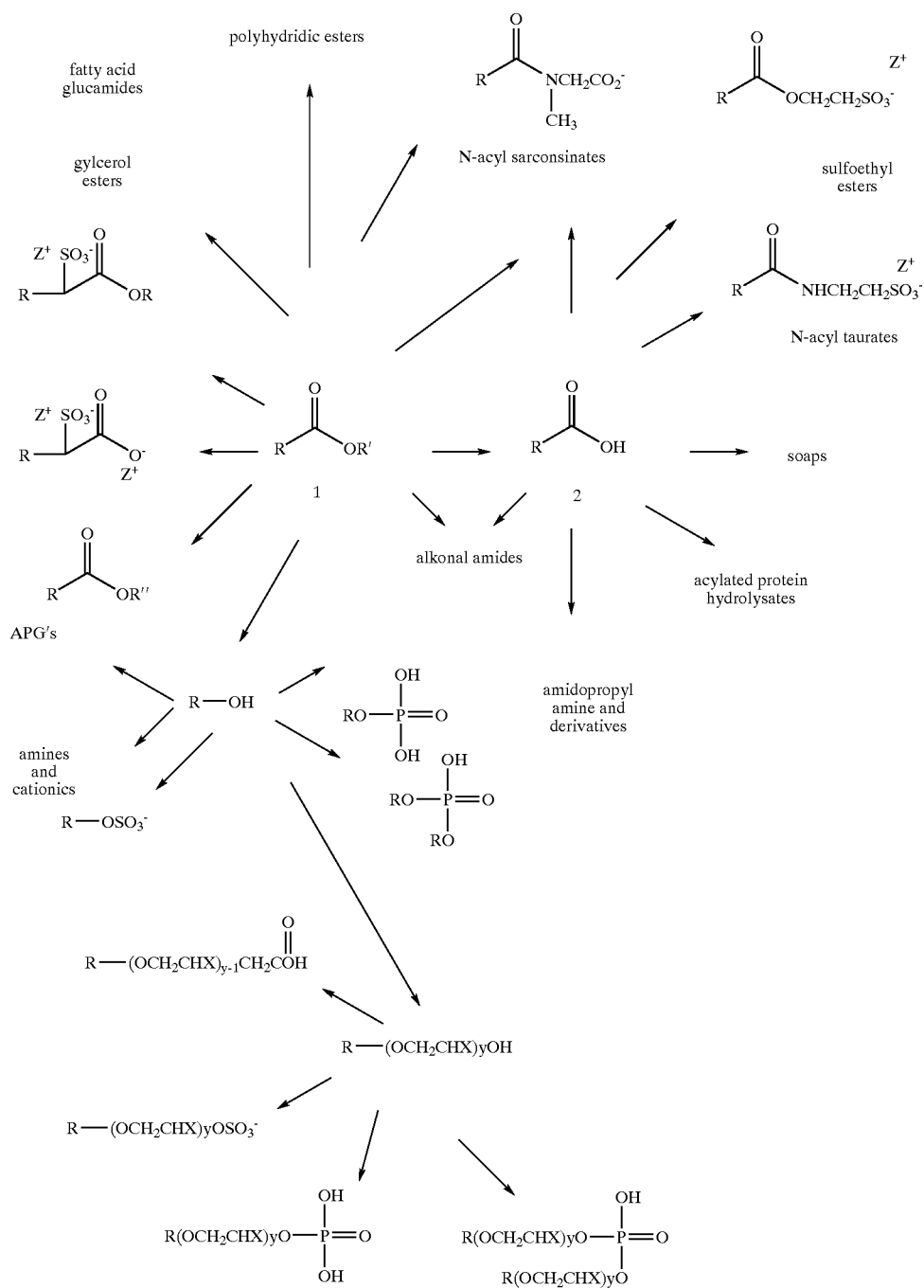

The invention will be illustrated by the following non-limiting examples.

EXAMPLE 1

Fatty Acid Ester Isomerization

Two grams of HBeta catalyst (Si/Al=25, extrudates) and 20 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of methyl oleate and the catalyst was heated up to 250° C. within 30 minutes and maintained for 5 h. After cooled down to room temperature within 20 minutes, the mixture was taken out of the reactor and the liquid product was separated from the solid catalyst by filtration.

NMR analysis shows that there was about 20 wt % acid formed in the product, as well as small amount of ketone and ester other than methyl ester. Methyl branching with an amount of 36.8 mol % and ethyl branching with an amount of 14.6 mol % were observed. There could be both branched methyl oleate and branched acid. Result of GC analysis is shown in Table 1.

EXAMPLE 2

Two grams of HBeta catalyst (Si/Al=25, powder), 20 g of methyl oleate and 2 g of $H_2O$ were loaded into a 135 ml autoclave reactor under nitrogen. After sealed, the reactor was purged with nitrogen. A nitrogen pressure of 50 psig was approached at room temperature. With an active stirring at 1000 RPM, the mixture was heated up to 250° C. within 30 minutes and maintained for 5 h. After cooled down to room temperature within 20 minutes, the mixture was taken out of the reactor and the liquid product was separated from the solid catalyst by filtration.

GC analysis (Table 1) showed higher conversion than the reaction in the absence of water. NMR analysis shows that the addition of water increased the conversion of methyl oleate, the yields of branched isomers (acid and/or ester) and free acid.

EXAMPLE 3

Two grams of $SO_4/ZrO_2$, and 10 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of toluene, methyl oleate and the catalyst was heated up to 250° C. within 30 minutes and maintained for 8 h. After cooled down to room temperature within 20 minutes, the mixture was taken out of the reactor and the liquid product was separated from the solid catalyst by filtration.

GC analysis (Table 1) shows that the conversion of methyl oleate is about 70 wt %. The product contains 29 wt % branched ester and/or acid and about 23 wt % aryl ester and/or acid (not shown in the table).

EXAMPLE 4

Two grams of HBeta catalyst (Si/Al=27, powder) and 20 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of methyl oleate and the catalyst was heated up to 250° C. within 30 minutes and maintained for 2 h. After cooled down to room temperature within 20 minutes, the mixture was taken out of the reactor and the liquid product was separated from the solid catalyst by filtration. Results based on GC analysis show that 78% of methyl oleate was isomerized. The product composition is shown in Table.

EXAMPLE 5

Two grams of $Cu^{2+}$ exchanged Beta catalyst (Si/Al=27, powder, 550° C. calcined in air) and 20 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of methyl oleate and the catalyst was heated up to 250° C. within 30 minutes and maintained for 2 h. After cooled down to room temperature within 20 minutes, the mixture was taken out of the reactor and the liquid product was separated from the solid catalyst by filtration. Results based on GC analysis show that 80% of methyl oleate was isomerized. The product composition is shown in Table.

EXAMPLE 6

0.4 g of HBeta catalyst (Si/Al=27, powder) and 40 g of methyl oleate were loaded into a 135 ml autoclave reactor under nitrogen. After sealed, the reactor was purged with nitrogen. A nitrogen pressure of 50 psig was approached at room temperature. With an active stirring at 1000 RPM, the mixture of methyl oleate and catalyst was heated up to 250° C. within 30 minutes and maintained for 7 h. After cooled down to room temperature within 20 minutes, the mixture was taken out of the reactor and the liquid product was separated from the solid catalyst by filtration. GC results are in Table 1.

EXAMPLE 7

0.8 g of HBeta catalyst (TOSOH, Si/Al=27, powder, 550° C. calcined in air) and 40 g of methyl oleate were loaded into a 135 ml autoclave reactor under nitrogen. After sealed, the reactor was purged three times with nitrogen. A nitrogen pressure of 50 psig was approached at room temperature. With an active stirring at 1000 RPM, the mixture of methyl oleate and catalyst was heated up to 280° C. within 30 minutes and maintained for 7 h. After cooled down to room temperature within 20 minutes, the mixture was taken out of the reactor and the liquid product was separated from the solid catalyst by filtration. GC results are in Table 1.

TABLE 1

| Example | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | other |
|---|---|---|---|---|---|---|---|---|---|---|---|---|---|
| Feed | 0.83 | 0.38 | 0 | 0.21 | 0.54 | 2.4 | 0.94 | 5.46 | 4.82 | 1.84 | 75.93 | 1.55 | 5.1 |
| 1 | 0.87 | 0.41 | 0.02 | 0.55 | 0.24 | 2.05 | 3.62 | 2.14 | 5.48 | 22.84 | 43.35 | 3.47 | 14.96 |
| 2 | 0.2 | 0.58 | 0.05 | 0.79 | 0.14 | 1.59 | 4.8 | 1.58 | 3.58 | 31.91 | 24.59 | 1.99 | 28.2 |
| 3 | 0.62 | 0.46 | 0.06 | 0.51 | 0.53 | 2.06 | 4.11 | 1.2 | 5.79 | 28.98 | 21.36 | 2.53 | 8.9 |
| 4 | 0.26 | 0.37 | 1.64 | 0.48 | 0.00 | 2.54 | 4.96 | 1.03 | 6.65 | 51.59 | 16.44 | 3.43 | 10.61 |
| 5 | 0.26 | 0.42 | 1.55 | 0.62 | 0.00 | 2.41 | 4.61 | 0.96 | 6.50 | 51.23 | 15.41 | 4.23 | 11.80 |
| 6 | 0.12 | 0.11 | 1.91 | 0.20 | 0.31 | 1.92 | 1.55 | 2.58 | 4.57 | 7.30 | 69.57 | 1.76 | 8.10 |
| 7 | 0.12 | 0.03 | 1.01 | 0.41 | 0.00 | 1.94 | 2.57 | 2.16 | 5.15 | 22.84 | 50.70 | 3.39 | 9.68 |

EXAMPLE 8

In a high throughput batch reactor system, two catalysts were tested. In each reactor, 0.05 g of catalyst and 1 g of methyl oleate were loaded. After sealed, the reactor system was purged with nitrogen. A nitrogen pressure of 100 psig was approached at room temperature. With an active stirring, the mixture of methyl oleate and the catalyst was heated up to 250° C. within 30 minutes and maintained for 7 h. After cooled down to room temperature within 20 minutes, the mixture was taken out of the reactor and the liquid product was separated from the solid catalyst by filtration. Table 2 lists these two catalysts. GC results are in Table 3.

TABLE 2

| Catalyst # | Name |
|---|---|
| 1 | HBeta(TRICAT) |
| 24 | HBeta(TOSOH) |

TABLE 3

| Catalyst # | <=$C_{10}$ | i-$C_{12}$ | $C_{12}$ | i$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | other |
|---|---|---|---|---|---|---|---|---|---|---|---|---|---|
| 1 | 0.04 | 0.14 | 3.09 | 0.44 | 0.00 | 1.63 | 4.41 | 0.69 | 6.53 | 48.20 | 15.97 | 3.87 | 14.99 |
| 24 | 0.06 | 0.16 | 2.84 | 0.52 | 0.05 | 2.02 | 3.93 | 0.96 | 6.04 | 43.45 | 24.49 | 3.23 | 12.25 |

We claim:

1. A branched fatty acid or alkyl ester thereof prepared by isomerizing a feedstock which comprises unsaturated linear fatty acids, alkyl esters of unsaturated fatty acids or mixtures thereof, wherein said process comprises subjecting said feedstock to an isomerization reaction in the presence of an acidic catalyst having a three-dimensional channel pore structure wherein at least one channel structure has a pore size diameter of at least 6 Å, wherein said acidic catalyst is not loaded with metal ions.

2. The branched fatty acid or alkyl ester thereof of claim 1 wherein said acidic catalyst comprises a zeolite, acidic clay, molecular sieve, or mixtures thereof.

3. The branched fatty acid or alkyl ester thereof of claim 2 wherein said acidic catalyst comprises a zeolite.

4. The branched fatty acid or alkyl ester thereof of claim 3 wherein said zeolite comprises at least one of the following framework structures: CON, DFO, FAU, AFS, AFY, BEA, BPH, EMT, GME, or mixtures thereof.

5. The branched fatty acid or alkyl ester thereof of claim 4 wherein the $SiO_2/Al_2O_3$ ratio of the zeolite is at least 2.

6. The branched fatty acid or alkyl ester thereof of claim 5 wherein said zeolite contains at least one channel structure having a pore diameter of at least 6.5 Å.

7. The branched fatty acid or alkyl ester thereof of claim 6 wherein said zeolite contains at least one channel structure having a pore diameter of at least 7 Å.

8. The branched fatty acid or alkyl ester thereof according to claim 1 wherein the feedstock comprises of at least 50% by weight of unsaturated fatty acids, alkyl esters of unsaturated fatty acids or mixtures thereof.

9. The branched fatty acid or alkyl ester thereof claim 8 wherein at least part of the isomerization is performed at a temperature of between 100° C. and 350° C.

10. The branched fatty acid or alkyl ester thereof of claim 9 wherein the amount of catalyst used is between 0.5 and 20% by weight of the feedstock in the batch reactor.

11. The branched fatty acid or alkyl ester thereof of claim 4 wherein said zeolite having a three-dimensional pore structure comprises at least one pore structure containing 10-membered rings as catalysts.

12. A derivative prepared from the branched fatty acid or alkyl ester thereof of claim 1 wherein said derivative is selected from the group consisting essentially of amphoteric, non-ionic, anionic and cationic surfactants.

13. The derivative of claim 12 wherein said derivative is selected from the group consisting essentially of fatty acid glucamides, glycerol esters, polyhydric esters, sulfoesters, sucrose esters, alpha sulfonates, N-acyl sarcosinates, acylated protein hydrolysates, acyl isethionates, amido propyl amine and derivatives thereof, alkanolamide, ethoxylated alkanolamides, nitriles, N-aryl taurates, soaps, esteramines, esterquats, alkyl polyglycosides (APGs), alcohol sulfates, phosphate esters, polyalkoxycarbonates and mixtures thereof.

14. The branched fatty acid or alkyl ester thereof of claim 4 wherein the $SiO_2/Al_2O_3$ ratio of the zeolite is at least 10.

* * * * *